(12) United States Patent
Cihlar

(10) Patent No.: US 6,479,231 B1
(45) Date of Patent: Nov. 12, 2002

(54) FLUORESCENCE-BASED ASSAY FOR THE INTERACTION OF SMALL MOLECULES WITH THE HUMAN RENAL ORGANIC ANION TRANSPORTER 1 (HOAT1)

(75) Inventor: Tomas Cihlar, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 56 days.

(21) Appl. No.: 09/721,104

(22) Filed: Nov. 22, 2000

Related U.S. Application Data

(60) Provisional application No. 60/167,436, filed on Nov. 23, 1999.

(51) Int. Cl.$^7$ .......................... H01N 61/00; C12Q 1/00; C07D 311/94
(52) U.S. Cl. ............................. 435/4; 514/1; 549/385
(58) Field of Search ........................ 514/1; 549/385; 435/4

(56) References Cited

PUBLICATIONS

Pritchard et al., "Mechanisms Mediating Renal Secretion of Organic Anions and Cations", 73(4):765–796, Physiol. Rev., 1993.

Pritchard et al., "Mechanisms mediating renal secretion of organic anions and cations", 73:765–796, Physiol. Rev., 1993.

Pritchard, J.B., "Rat renal cortical slices demonstrate p–aminohippurate/glutarate exchange and sodium/glutarate coupled p–aminohippurate transport", 255:969–975, J. Pharmacol. Exp. Ther., 1990.

Pritchard, J.B., "Coupled transport of p–aminohippurate by rat kidney basolateral membrane vesicles", 255:F597–F604, Am J Physiol, 1988.

Roche–Ramel, F., "Renal Transport of Organic Anions", 7:517–524, Curr. Opin. Nephrol. Hypertens., 1998.

Sekine et al., "Expression Cloning and Characterization of a Novel Multispecific Organic Anion Transporter", 272(30):18526–18529, J Biol Chem, Jul. 25, 1997.

Stieger et al., "Bile acid and xenobiotic transporters in liver", 10:462–467, Curr. Opp. Cell Biol., 1998.

Sullivan et al., "Specificity of basolateral organic anion exchanger in proximal tubule for cellular and extracellular solutes", 2(7):1192–1200, J. Am. Soc. Nephrol., 1992.

Sullivan et al., "Fluorescein transport in isolated proximal tubules in vitro: epifluorometric analysis", 258:F46–F51, Am J Physiol, 1990.

Sweet et al., "Expression Cloning and Characterization of ROAT1", 272(48):30088–30095, J Biol Chem, Nov. 28, 1997.

Sweet et al., "The molecular biology of renal organic anion and cation transporters", 31:89–118, Cell Biochem. Biophys., 1999.

Tojo et al., "Immunohistochemical Localization of Multispecific Renal Organic Anion Transporter 1 in Rat Kidney", 10:464–471, J. Am. Soc. Nephrol., 1999.

Tsuda et al., "Transport of ochratoxin A by renal multispecific organic anion transporter 1", 289(3):1301–1305, J. Pharmacol. Exp. Ther., 1999.

Tune, B.M., "Nephrotoxicity of beta–lactam antibiotics: mechanisms and strategies for prevention", 11:768–772, Pediatr. Nephrol., 1997.

Ullrich et al., "Contraluminal transport systems in the proximal renal tubule involved in secretion of organic anions", 254:F453–F462, Am J Physiol, 1988.

Ullrich et al., "Contraluminal para–aminohippurate transport in the proximal tubule of the rat kidney", 413:134–146, Pfluegers Arch., 1988.

Ullrich et al., "Renal transport mechanisms for xenobiotics: chemicals and drugs", 71:843–848, Clin. Investig., 1993.

Apiwattanakul et al., "Transport Properties of Nonsteroidal Anti–Inflammatory Drugs by Organic Anion Transporter 1 Expressed in Xenopus laevis Oocytes", 55:847–854, Mol Pharm, 1999.

Cihlar et al., "The antiviral nucleotide analogs cidofovir and adefovir are novel substrates for human and rat renal organic anion transporter 1", 56:570–580, Mol Pharm, 1999.

Edwards et al., "Transport of [3H]losartan across isolated perfused rabbit proximal tubule", 290(1):38–42, J. Pharmacol. Exp. Ther., 1999.

(List continued on next page.)

Primary Examiner—Alan L. Rotman
Assistant Examiner—Raymond Covington
(74) Attorney, Agent, or Firm—Max D. Hensley

(57) ABSTRACT

Secretion of small molecules from systemic blood circulation into urine is one of the physiologically essential functions of the kidney. Human organic anion transporter (hOAT1) is a key component in the renal tubular secretion of negatively charged molecules including a variety of important therapeutics. In some cases, compounds interacting with hOAT1 may induce pharmacokinetic drug-drug interactions or cause nephrotoxicity. We developed a fluorescence-based, 96-well format assay using CHO cells stably expressing hOAT1, which allows for the evaluation of interactions between small molecules and hOAT1. The assay is based on the inhibition of the transport of 6-carboxyfluorescein, a high-affinity hOAT1 substrate ($K_m$ = 3.9 $\mu$M), which was identified among several other fluorescent organic anions. The relative inhibition potency of various known hOAT1 substrates determined using the 6-carboxyfluorescein-based inhibition assay correlated well with their $K_m$ values, indicating that the fluorescent assay exhibits a proper specificity. This in vitro assay can be employed to evaluate the mechanism of renal clearance of organic anions, to assess the potential induction of drug-drug interactions and/or nephrotoxic effects of various therapeutics, and to screen for novel hOAT1 inhibitors that could serve as efficient nephroprotectants.

18 Claims, 5 Drawing Sheets

OTHER PUBLICATIONS

Figure 1:
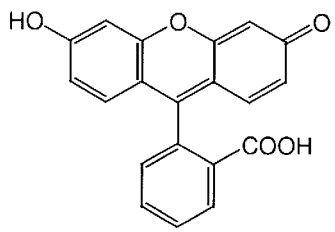
Figure 1:
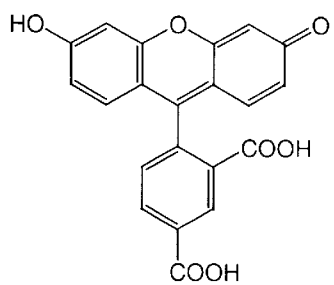
Figure 1:
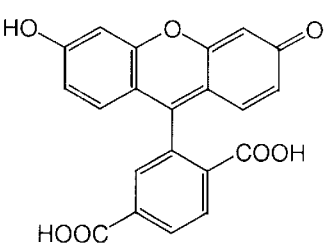
Figure 1:
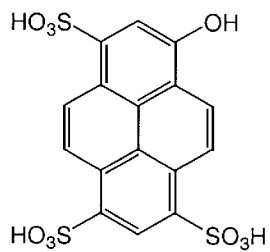
Figure 1:
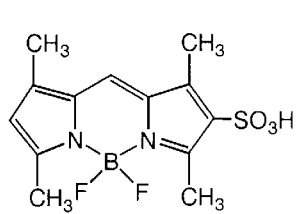
Figure 1:
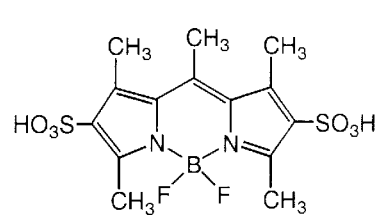

Fritzsch et al., "Anion transport through the contraluminal cell membrane of renal proximal tubule. The influence of hydrophobicity and molecular charge distribution on the inhibitory acivity of organic anions", 978:249–256, Biochem Biophys Acta, 1989.

Ho et al., "Cytotoxicity of Antiviral Nucleotides Adefovir and Cidofovir Is Induced by the Expression of Human Renal Organic Anion Transporter 1", 11:383–393, J. Am. Soc. Nephrol., 1999.

Holy et al., "Synthesis of 9-(2-Phosphonylmethoxyethyl)Adenine and Related Compounds", 52:2801–2809, Collect Czech Chem Commun, 1987.

Hosoyamada et al., "Molecular cloning and functional expression of a multispecific organic anion transporter from human kidney", 276:F122–F128, Am J Physiol, 1999.

Jariyawat et al., "The interaction and transport of beta–lactam antibiotics with the cloned rat renal organic anion transporter 1", 290(2):672–677, J. Pharmacol. Exp.Ther., 1999.

Lu et al., "Cloning of the human kidney PAH transporter: narrow substrate specificity and regulation by protein kinase C", 276:F295–F303, Am J Physiol, 1999.

Pritchard et al., "Renal secretion of organic anions and cations", 49:1649–1654, Kidney International, 1996.

Villalobos et al., "Mechanism mediating basolateral transport of 2,4–dichlorophenoxyacetic acid in rat kidney", 278(2):582–589, J. Pharmacol. Exp. Ther., 1996.

Fluorescein
λ(Abs) = 490 nm
λ(Em) = 525 nm

5-Carboxyfluorescein
λ(Abs) = 490 nm
λ(Em) = 525 nm

6-Carboxyfluorescein
λ(Abs) = 490 nm
λ(Em) = 525 nm

Pyranine
λ(Abs) = 454 nm
λ(Em) = 510 nm

BODIPY 495/505 sulfonate
λ(Abs) = 500 nm
λ(Em) = 520 nm

BODIPY 492/515 disulfonate
λ(Abs) = 490 nm
λ(Em) = 515 nm

FLUORESCENCE-BASED ASSAY FOR THE INTERACTION OF SMALL MOLECULES WITH THE HUMAN RENAL ORGANIC ANION TRANSPORTER 1 (HOAT1)

CROSS REFERENCED TO RELATED APPLICATIONS

This application is based upon United States Provisional Application Ser. No. 60/167,436 filed Nov. 23, 1999. It is related to pending United States Patent Application Ser. No. 09/330,245, filed June 10, 1999, relating to hOAT1 and its uses. Both applications are expressly incorporated by reference.

INTRODUCTION

Organic anion transporter (OAT) is an essential component of the renal tubular secretory pathway of small negatively charged molecules (1). OAT, which is located in the basolateral (anti-luminal) membrane of renal proximal convoluted tubules (2), mediates the active uptake of anionic substrates from the systemic blood circulation into the proximal tubular epithelium and functions in concert with luminal (apical) efflux carrier(s) or channel(s) (3). Biochemical studies using the renal cortical slices, intact tubules, or basolateral membrane vesicles isolated from the renal cortex have provided initial information on the function and substrate specificity of the OAT system (4, 5, 6). Recent cloning of OAT from several species including human (hOAT1) accelerated further characterization of this physiologically important membrane transport protein (7, 8, 9). Upon heterologous functional expression in *Xenopus laevis* oocytes, OAT variants from different species have shown the ability to transport p-aminohippuric acid (PAH), a prototypical organic anion substrate, in exchange for intracellular dicarboxylate (e.g. (α-ketoglutarate, glutarate) (9, 10). Subsequent studies revealed a broad substrate specificity for OAT, which includes endogenous metabolites (urate), signal molecules (cyclic nucleotides, prostaglandins), toxins (ochratoxin A), as well as xenobiotics (2,4-dichlorophenoxyacetic acid) (11, 12, 13). In addition, recent studies indicated that the OAT system is involved in the tubular secretion of many important therapeutics such as β-lactam antibiotics (14), nonsteroidal anti-inflamatory drugs (15), antiviral nucleotide analogs (9), and non-peptidic angiotensin inhibitors (16). It has been postulated that in some cases, compounds transported by the OAT system may induce pharmacokinetic drug-drug interactions or cause nephrotoxicity (17, 18). In the past, the evaluation of potential OAT substrates and/or inhibitors has been restricted to inhibition assays using the isolated renal tubules or basolateral membrane vesicles and radioactive OAT substrates (most frequently PAH) (4, 19, 20). Although more recent approaches have relied on the transport assays in Xenopus oocytes transiently expressing rat OAT or hOAT1 (9, 14, 15), there was no straightforward, efficient, and reproducible assay available for OAT transport activity. In this study, we describe the development of a fluorescent cell-based assay, which allows for an efficient and reliable evaluation of the interaction between small molecules and hOAT1.

SUMMARY OF THE INVENTION

The method of this invention comprises contacting isolated hOAT1 with a compound having formula I

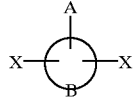

wherein A is a detectable group, B is a saturated or unsaturated heterocycle or carbocycle containing 6 ring atoms, X independently is —(R$_1$)nY, where n independently is 0 or 1, R$_1$ is —CR$_2$R$_3$; R$_2$ and R$_3$ independently are hydrogen, halo, nitro, or C$_1$–C$_2$ alkyl, and Y is carboxyl or aldehyde; wherein B is unsubstituted other than by X or is substituted with X and with R$_2$; and wherein the —(R$_1$)nY groups are positioned para to one another.

Materials and Methods

Stably Transfected Cell Lines

CHO$^{hOAT}$ and CHO$^{pIRES}$ cell lines were generated by stable transfection of hOAT1 cDNA and the empty pIRESneo expression vector (Stratagene, La Jolla, Calif.), respectively, into Chinese hamster ovary cells. The procedure, as well as detailed characterization of both cell lines is described elsewhere (18). The cells were maintained in phenol red-free F-12 nutrient mixture supplemented with 10% fetal bovine serum and 1 mg/ml G-418. Cells for direct use in the experiments were grown in the absence of G-418.

Reagents

Fluorescein, 5-carboxyfluorescein, and 6-carboxyfluorescein were obtained from Sigma (St. Louis, Mo.). 8-hydroxypyrene-1,3,6-trisulfonic acid (pyranine), BODIPY 492/515 disulfonate, and BODIPY 495/505 sulfonate were from Molecular Probes (Eugene, Oreg.). [$^3$H] PAH (3.7 Ci/mmol) was from Dupont NEN (Boston, Mass.) and [$^{14}$C]glutaric acid (55 mCi/mmol) from American Radiolabaled Chemicals (St. Louis, Mo.). [$^3$H]9-(2-phosphonylmethoxyethyl)adenine (adefovir; 30 Ci/mmol), [$^{14}$C](S)-1-(3-hydroxy-2-phosphonylmethoxypropyl)cytosine (cidofovir; 56 mCi/mmol) and [$^{14}$C] [((S)-1-2-hydroxy-2-oxo-1,4,2-dioxaphosphorinan-5-yl)methyl]cytosine (cyclic prodrug of cidofovir; 55 mCi/mmol) were prepared by Moravek Biochemicals (Brea, Calif.). Adefovir, cidofovir, and cyclic prodrug of cidofovir were synthesized at Gilead Sciences according to previously published procedures (21). All other chemicals were obtained from Sigma at the highest purity available.

The fluorophore group A is any moiety which is detectable by fluorescence assay, be that absorption or emission. Typical the fluorophore is

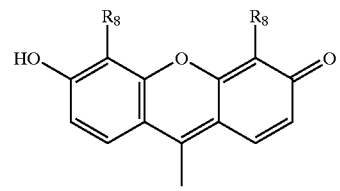

wherein R$_8$ is R$_4$ or R$_7$; R$_4$ is C$_1$–C$_3$ alkyl and R$_7$ is hydrogen or —CH$_2$N(CH$_2$COOH)$_2$;

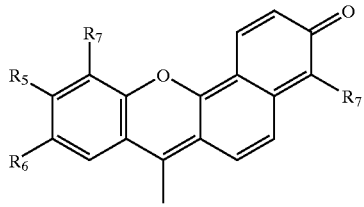

wherein $R_5$ is hydroxyl or $-N(R_4)_2$ and $R_6$ is hydrogen or halogen, $R_7$ is hydrogen or $-CH_2N(CH_2COOH)_2$; or

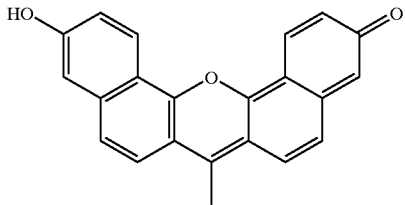

However, it will be understood that other known chromophore or fluorophore labels used heretofore as analytic tags will be suitable as "A" groups.

The group

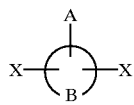

generally is phenyl or phenyl in which one ring carbon atom is substituted by O, NH or S, but typically has structure III

III

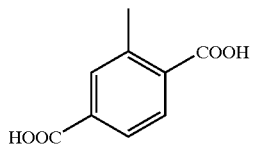

Ordinarily X is carboxyl, but also may be aldehyde.

Fluorescent Transport Assay $CHO^{hOAT}$ or $CHO^{pIRES}$ cells were seeded into 96-well plates at a density of $3 \times 10^4$ cells/well. After 48 hours, the cells were washed once with phosphate-buffered saline (PBS) and then incubated at room temperature in the presence of Waymouth buffer (135 mM NaCl, 5 mM KCl, 2.5 mM $CaCl_2$, 1.2 mM $MgCl_2$, 0.8 mM $MgSO_4$, 28 mM glucose, and 13 mM HEPES pH 7.2) containing the fluorescent substrate. Cellular uptake was terminated by washing the wells 3-times with 200 μl ice-cold PBS. Subsequently, the cells were lysed with 200 μl 0.4% Triton X-100 in 20 mM Tris-HCl, pH 9.0, for 30 min at room temperature. The lysates were transferred into MICROFLUOR2 96-well plates (DYNEX, Chantilly, Va.) and the fluorescence was determined using Spectra-Max Gemini 96-well plate fluorescence reader (Molecular Devices, Sunnyvale, Calif.). To determine $IC_{50}$ (50% inhibitory concentration) values in the inhibition assay, 4-fold serial dilutions of the tested compounds were prepared in triplicates in a separate 96-well plate and mixed with an equal volume of 8 μM 6-carboxyfluorescein. The uptake was initiated by adding the premixed samples to PBS-washed cells. The final concentration of substrate in the assay was equal to its $K_m$ (4 μM). After 5 min at room temperature, the incubation was terminated and intracellular fluorescence determined as above. $IC_{50}$ values were estimated from semilogarithmic plots of the inhibitor concentration vs. percentage of net uptake relative to the uninhibited control.

Transport Kinetics with the Radioactive Substrates

The assays were carried out in 12-well plates with nearly confluent cells seeded 48 hours prior to each experiment. Immediately before the experiment, the cells were washed with PBS pre-warmed to 37° C. Pre-warmed Waymouth buffer (450 l/well) containing radiolabeled substrate at various concentrations was added to the cells and incubated for 3 min at 37° C. At the end of incubation, the cells were washed 3-times with ice-cold PBS (2 ml/well) and lysed directly on the plate in the presence of 0.4% Triton X-100 (0.5 ml/well) for at least 20 min. Subsequently, the wells were washed with an additional 0.5 ml of the detergent, the lysate and wash were combined, and radioactivity in each sample was determined after adding 6 ml of scintillation fluid (Beckman Instruments, Fullerton, Calif.). $K_m$ values were estimated by the linear regression from double reciprocal plots using Enzyme Kinetics software (ChemSW, Fairfield, Calif.).

Results and Discussion

Transport of Fluorescent Organic Anions by hOAT1

Recently, we described a generation of $CHO^{hOAT}$ cells stably transfected with hOAT1 cDNA (18). The cells are capable of accumulating hOAT1 substrates to levels 30- to 50-fold higher than those detected in $CHO^{pIRES}$ cells stably transfected with the empty expression vector. The expressed transporter exhibits the expected substrate specificity as well as susceptibility to inhibitors, and functions as an organic anion/dicarboxylate exchanger (18). We used $CHO^{hOAT}$ cells to develop an assay that can be utilized for evaluation of the affinity of tested molecules towards hOAT1.

It has been demonstrated earlier that renal proximal tubules are able to accumulate fluorescein (22). The accumulation was inhibited by probenecid and various organic anions (23), suggesting that fluorescein and possibly some other fluorescent anions may be substrates for the OAT system and, thus, serve as suitable probes to assess hOAT1 transport activity. Therefore, several fluorescent organic anions were evaluated for their hOAT1-mediated transport. Their structures as well as parameters used to determine their fluorescent signal are given in FIG. 1. In addition to fluorescein, accumulation of two fluorescein derivatives (5- and 6-carboxyfluorescein; 5- and 6-CFL) and three fluorescent aromatic mono- and polysulfonic acids was measured in $CHO^{hOAT}$ cells and control $CHO^{pIRES}$ cells in the absence or presence of probenecid (FIG. 2). None of the three sulfonic acids showed any evidence of hOAT1-mediated transport. In contrast, fluorescein showed approximately 2-fold higher accumulation in $CHO^{hOAT}$ cells than in control $CHO^{pIRES}$ cells. Probenecid only partly inhibited the uptake of fluorescein into $CHO^{hOAT}$ cells suggesting the presence of both hOAT1-specific and non-specific transport. 5-CFL accumulated at very low levels both in $CHO^{hOAT}$ and $CHO^{pIRES}$ cells. However, 6-CFL was taken up by $CHO^{hOAT}$ cells approximately 15-fold more efficiently than by $CHO^{pIRES}$ control cells. In the presence of probenecid, the accumulation of 6-CFL in $CHO^{hOAT}$ cells was comparable to that detected in $CHO^{pIRES}$ cells. Altogether, these characteristics indicate an efficient hOAT1-specific transport of 6-CFL and underline the striking difference between the two CFL isomers.

Previously, it has been shown that the interaction of various aliphatic dicarboxylic acids with rat OAT is greatly affected by the distance between the negative charges. In that study, glutarate showed the highest affinity for the OAT system of all aliphatic dicarboxylates (24). Notably, dicarboxylic acids shorter by one or more carbons did not show any interaction with OAT. The lack of the interaction between 5-CFL and hOAT1 indicates that the requirement for a specific distance between the two negative charges in a dicarboxylate molecule, which allows for an efficient interaction with the OAT system, can be extended beyond the class of aliphatic dicarboxylic acids. In contrast, dicarboxylic acids longer than glutarate by one or more carbon still retained the capability of interacting with OAT, presumably due to a presence of hydrophobic interactions between the dicarboxylate backbone and OAT binding site (24). Thus, hydrophobic interactions may also play a role in the proper positioning of 6-CFL within the binding site of hOAT1 resulting in its efficient transport.

Characterization of 6-CFL Transport by hOAT1

Figure 3:
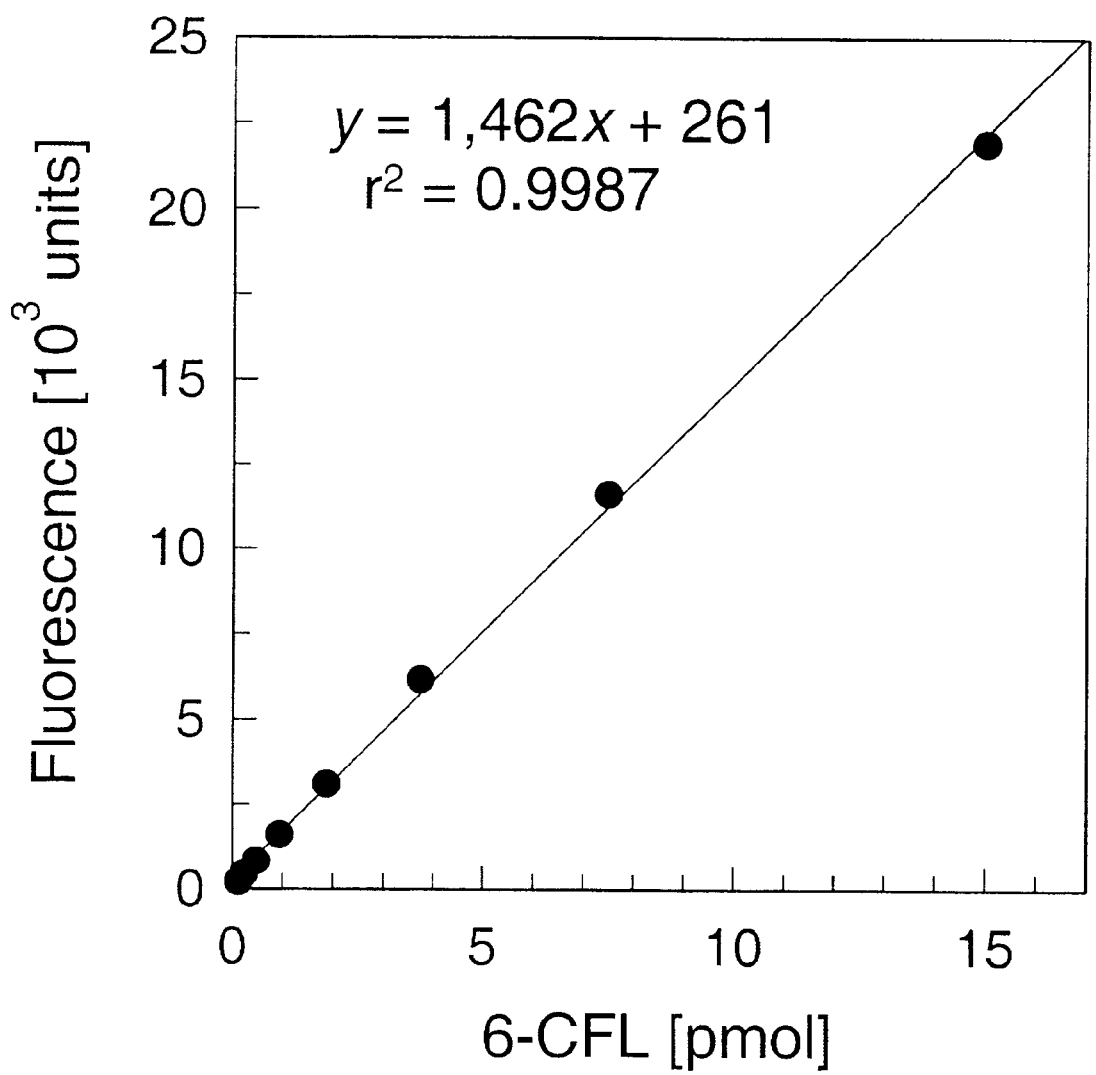

As demonstrated by the calibration curve in FIG. 3, the fluorescent signal of 6-CFL in the cell lysis buffer showed a linear increase in the range from 0.1 to at least 15 pmol. To determine the affinity of 6-CFL towards hOAT1, kinetic parameters of the transport were analyzed. The high efficiency and low background of hOAT1-mediated transport of 6-CFL allowed these experiments to be performed in the 96-well format at room temperature. First, a time-course of hOAT1-specific uptake of 6-CFL at various concentrations ranging from 0.31 to 20 $\mu$M was determined. As illustrated in FIG. 4a, the intracellular accumulation of 6-CFL via hOAT1 shows an approximately linear time-dependence during the first 4 minutes of the incubation. Hence, 2-min and 4-min endpoints could be used to estimate the kinetic constants for hOAT1-specific transport of 6-CFL. Using the 4-min endpoints, $K_m$ and $V_{max}$ values of 3.93 $\mu$M and 17.8 pmol/$10^6$ cells·min, respectively, were estimated from a double reciprocal plot (FIG. 4b). Data from the 2-min endpoinds yielded almost identical values ($K_m$=3.95 $\mu$M and $V_{max}$=19.7 pmol/$10^6$ cells·min). Notably, these kinetic parameters account for a transport efficiency (i.e. Vmax/Km ratio) comparable to that of PAH, the prototype hOAT1 substrate (18).

Figure 5:
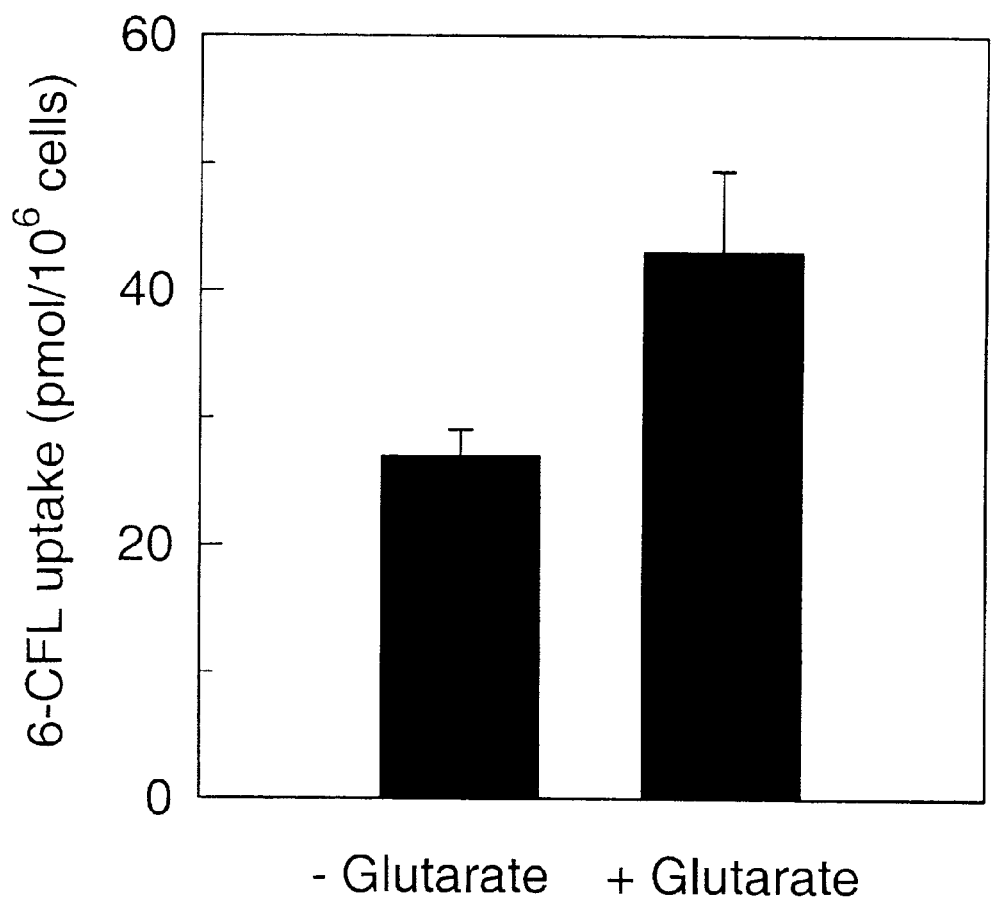

Similar to PAH (18), the uptake of 6-CFL into CHO$^{hOAT}$ was stimulated by preloading the cells with glutarate, which functions as an intracellular counter-ion for the hOAT1-mediated anion exchange. Pre-incubation of CHO$^{hOAT}$ cells with 1.25 mM glutarate for 2 hours increased the subsequent intracellular accumulation of 6-CFL by approximately 60% (FIG. 5). This finding indicates that the transport of 6-CFL is based on the same anion-exchange mechanism as that of the other known hOAT1 substrates.

Specificity of the Fluorescence-based Assay

In the past, the affinity of small molecules for the renal OAT system has usually been assessed by the inhibition assays with suitable radiolabeled substrates, e.g. PAH (19, 20). Given the high-affinity transport of 6-CFL by hOAT1, this fluorescent anion may be used as an efficient and convenient probe, which may substitute for the radiolabeled substrates. To evaluate the specificity of the fluorescent assay, a variety of known substrates and inhibitors of the OAT system were tested for their inhibition of 6-CFL transport in CHO$^{hOAT}$ cells. In addition, the transport kinetics of the corresponding radiolabeled substrates was directly measured in CHO$^{hOAT}$ cells and the $K_m$ values were compared with the relative inhibition potency obtained from the 6-CFL-based assay. PAH and glutarate, two high-affinity hOAT1 substrates, were among the most potent inhibitors of 6-CFL uptake exhibiting $IC_{50}$ values of 15.4 and 10.7 $\mu$M, respectively (Table 1). Nonsteroidal anti-inflammatory drugs (salicylate and ketoprofen), antiviral nucleotide analogs (adefovir, cidofovir, and its cyclic prodrug), and β-lactam antibiotics (cephaloridine and cephradine), all of which have been shown to interact with the OAT system (9, 14, 15), also inhibited the transport of 6-CFL. In accordance with previous findings (14), β-lactams showed the weakest inhibition potency. In contrast, ketoprofen was the most potent inhibitor among the tested compounds with $IC_{50}$ of 1.4 $\mu$M. This correlates with recent observations from inhibition assays in Xenopus oocytes expressing rat OAT (15). As expected, the cationic compound N-methylnicotinamide, which is a substrate for renal organic cation transporter (25), but not for OAT, did not interfere with the transport of 6-CFL. Overall, the inhibition potency of the tested hOAT1 substrates in the 6-CFL-based assay was proportional to their $K_m$ values, indicating that the fluorescent inhibition assay exhibits a specificity comparable to that of the direct transport kinetic assays utilizing radiolabeled substrates.

In summary, we developed a convenient 96-well plate fluorescence-based assay that simplifies and accelerates the evaluation of potential substrates and/or inhibitors of hOAT1. Given the physiological importance of hOAT1, this assay can be utilized to assess the mechanism of renal secretion of small molecules, their potential nephrotoxic effects and/or pharmacokinetic drug-drug interactions, and to screen for novel hOAT1 inhibitors that could serve as efficient nephroprotective agents.

Recently, remarkable progress has been achieved in the identification and characterization of a number of novel membrane transport proteins expressed in specific organs, tissues, or cell types (26, 27). It is now obvious that the active membrane transport plays a critical role in the absorption and secretion of many important therapeutics, their distribution into different body compartments, induction of drug-related organ-specific toxicities, and in some cases also in the protection of organs against drug-associated toxic effects. Hence, it might be expected that the characterization of a broad range of transport interactions will soon become a standard part of the drug development process requiring a spectrum of specific and efficient transport assays similar to the described fluorescence-based hOAT1 assay.

Citations

1. Roch-Ramel, F. (1998) Renal transport of organic anions. Curr. Opin. Nephrol. Hypertens. 7, 517–524.
2. Tojo, A., Sekine, T., Nakajima, N., Hosoyamada, M., Kanai, Y., Kimura, K., and Endou, H. (1999) Immunohistochemical Localization of Multispecific Renal Organic Anion Transporter 1 in Rat Kidney. J. Am. Soc. Nephrol. 10, 464–471.
3. Pritchard, J. B. and Miller, D. S. (1993) Mechanisms mediating renal secretion of organic anions and cations. Physiol. Rev. 73, 765–96.
4. Ullrich, K. J., Rumrich, G., and Kloss, S. (1988) Contraluminal para-aminohippurate transport in the proximal tubule of the rat kidney. IV. Specificity: mono- and polysubstituted benzene analogs. Pfluegers Arch. 413, 134–146.
5. Pritchard, J. B. (1988) Coupled transport of p-aminohippurate by rat kidney basolateral membrane vesicles. Am. J. Physiol. 255, F597–604.
6. Pritchard, J. B. (1990) Rat renal cortical slices demonstrate p-aminohippurate/glutarate exchange and sodium/glutarate coupled p-aminohippurate transport. J. Pharmacol. Exp. Ther. 255, 969–975.
7. Hosoyamada, M., Sekine, T., Kanai, Y., and Endou, H. (1999) Molecular cloning and functional expression of a multispecific organic anion transporter from human kidney. *Am. J. Physiol.* 276, F122-F128.
8. Lu, R., Chan, B. S., and Schuster, V. L. (1999) Cloning of the human kidney PAH transporter: narrow substrate specificity and regulation by protein kinase C. *Am. J. Physiol.* 276, F295-F303.
9. Cihlar, T., Lin, D. C., Pritchard, J. B., Fuller, M. D., Mendel, D. B., and Sweet, D. H. (1999) The antiviral nucleotide analogs cidofovir and adefovir are novel substrates for human and rat renal organic anion transporter 1. *Mol. Pharmacol.* 56, 570–580.
10. Sweet, D., Wolff, N., and Pritchard, J. (1997) Expression Cloning and Characterization of hOAT1. *J. Biol. Chem.* 272, 30088–30095.
11. Sekine, T., Watanabe, N., Hosoyamada, M., Kainai, Y., and Endou, H. (1997) Expression Cloning and Characterization of a Novel Multispecific Organic Anion Transporter. *J. Biol. Chem.* 272, 18526–18529.
12. Villalobos, A. R., Dunnick, C. A., and Pritchard, J. B. (1999) Mechanism mediating basolateral transport of 2,4-dichlorophenoxyacetic acid in rat kidney. *J. Pharmacol. Exp. Ther.* 278, 582–9.
13. Tsuda, M., Sekine, T., Takeda, M., Cha, S. H., Kanai, Y., Kimura, M., and Endou, H. (1999) Transport of ochratoxin A by renal multispecific organic anion transporter 1. *J. Pharmacol. Exp. Ther.* 289, 1301–5.
14. Jariyawat, S., Sekine, T., Takeda, M., Apiwattanakul, N., Kanai, Y., Sophasan, S., and Endou, H. (1999) The interaction and transport of beta-lactam antibiotics with the cloned rat renal organic anion transporter 1. *J. Pharmacol. Exp. Ther.* 290, 672–7.
15. Apiwattanakul, N., Sekine, T., Chairoungdua, A., Kanai, Y., Nakajima, N., Sophasan, S., and Endou, H. (1999) Transport properties of nonsteroidal anti-inflammatory drugs by organic anion transporter 1 expressed in Xenopus laevis oocytes. *Mol. Pharmacol.* 55, 847–854.
16. Edwards, R. M., Stack, E. J., and Trizna, W. (1999) Transport of [3H]losartan across isolated perfused rabbit proximal tubule. *J. Pharmacol. Exp. Ther.* 290, 38–42.
17. Tune, B. M. (1997) Nephrotoxicity of beta-lactam antibiotics: mechanisms and strategies for prevention. *Pediatr. Nephrol.* 11, 768–772.
18. Ho, E. S., Lin, D. S., Mendel, D. B., and Cihlar, T. (1999) Cytotoxicity of Antiviral Nucleotides Adefovir and Cidofovir Is Induced by the Expression of Human Renal Organic Anion Transporter 1. *J. Am. Soc. Nephrol.*, in press.
19. Ullrich, K. J. and Rumrich, G. (1988) Contraluminal transport systems in the proximal renal tubule involved in secretion of organic anions. *Am. J. Physiol.* 254, F453-F462.
20. Ullrich, K. J. and Rumrich, G. (1993) Renal transport mechanisms for xenobiotics: chemicals and drugs. *Clin. Investig.* 71, 843–8.
21. Holy, A. and Rosenberg, I. (1987) Synthesis of 9-(2-phosphonylmethoxyethyl)-adenine and related compounds. *Coll. Czech. Chem. Commun.* 52, 2801–2809.
22. Sullivan, L. P., Grantham, J. A., Rome, L., Wallace, D., and Grantham, J. J. (1990) Fluorescein transport in isolated proximal tubules in vitro: epifluorometric analysis. *Am. J. Physiol.* 258, F46-F51.
23. Sullivan, L. P. and Grantham, J. J. (1992) Specificity of basolateral organic anion exchanger in proximal tubule for cellular and extracellular solutes. *J. Am. Soc. Nephrol.* 2, 1192–1200.
24. Fritzsch, G., Rumrich, G., and Ullrich, K. J. (1989) Anion transport through the contraluminal cell membrane of renal proximal tubule. The influence of hydrophobicity and molecular charge distribution on the inhibitory activity of organic anions. *Biochim. Biophys. Acta* 978, 249–256.
25. Pritchard, J. B. and Miller, D. S. (1996) Renal secretion of organic anions and cations. *Kidney International* 49, 1649–1654.
26. Sweet, D. H. and Pritchard, J. B. (1999) The molecular biology of renal organic anion and cation transporters. *Cell Biochem. Biophys.* 31, 89–118.
27. Stieger, B. and Meier, P.J. (1998) Bile acid and xenobiotic transporters in liver. *Curr. Opp. Cell Biol.* 10, 462–467.

TABLE 1

Interaction of small molecules with hOAT1:
Comparison of the fluorescence-
based inhibition assay with the direct
transport assay using radioactive substrates

| Compound | $IC_{50}$ [$\mu$M]$^A$ | $K_m$ [$\mu$M]$^B$ |
| --- | --- | --- |
| PAH | 8.8 ± 1.6 | 15.4 ± 2.5 |
| Glutarate | 4.9 ± 0.6 | 10.7 ± 1.6 |
| Salicylate | 280 ± 42 | n.d.$^C$ |
| Ketoprofen | 1.4 ± 0.2 | n.d. |
| Adefovir | 28 ± 2.8 | 23.8 ± 4.2 |
| Cidofovir | 60 ± 3.9 | 58.0 ± 5.7 |
| Cyclic prodrug of cidofovir | 1,100 ± 280 | 309 ± 106 |
| Cephaloridine | 1,250 ± 420 | n.d. |
| Cephradine | 1,600 ± 280 | n.d. |
| Probenecid | 6.3 ± 0.4 | 4.3 ± 1.5 ($K_i$)$^D$ |
| N-methylnicotinamide | >>2,000 | n.a.$^E$ |

$^A$Inhibition of the hOAT1-specific transport of 4 $\mu$M 6-CFL. The data represent mean ± standard error from two independent experiments.
$^B$Transport kinetics was determined using the radiolabeled substrates. The data represent mean ± standard error from three to five independent experiments.
$^C$n.d. = not determined.
$^D$Inhibition constant $K_i$ determined against the hOAT1-mediated uptake of [$^3$H]PAH.
$^E$n.a. = not applicable.

Figure Legends

Figure 2:
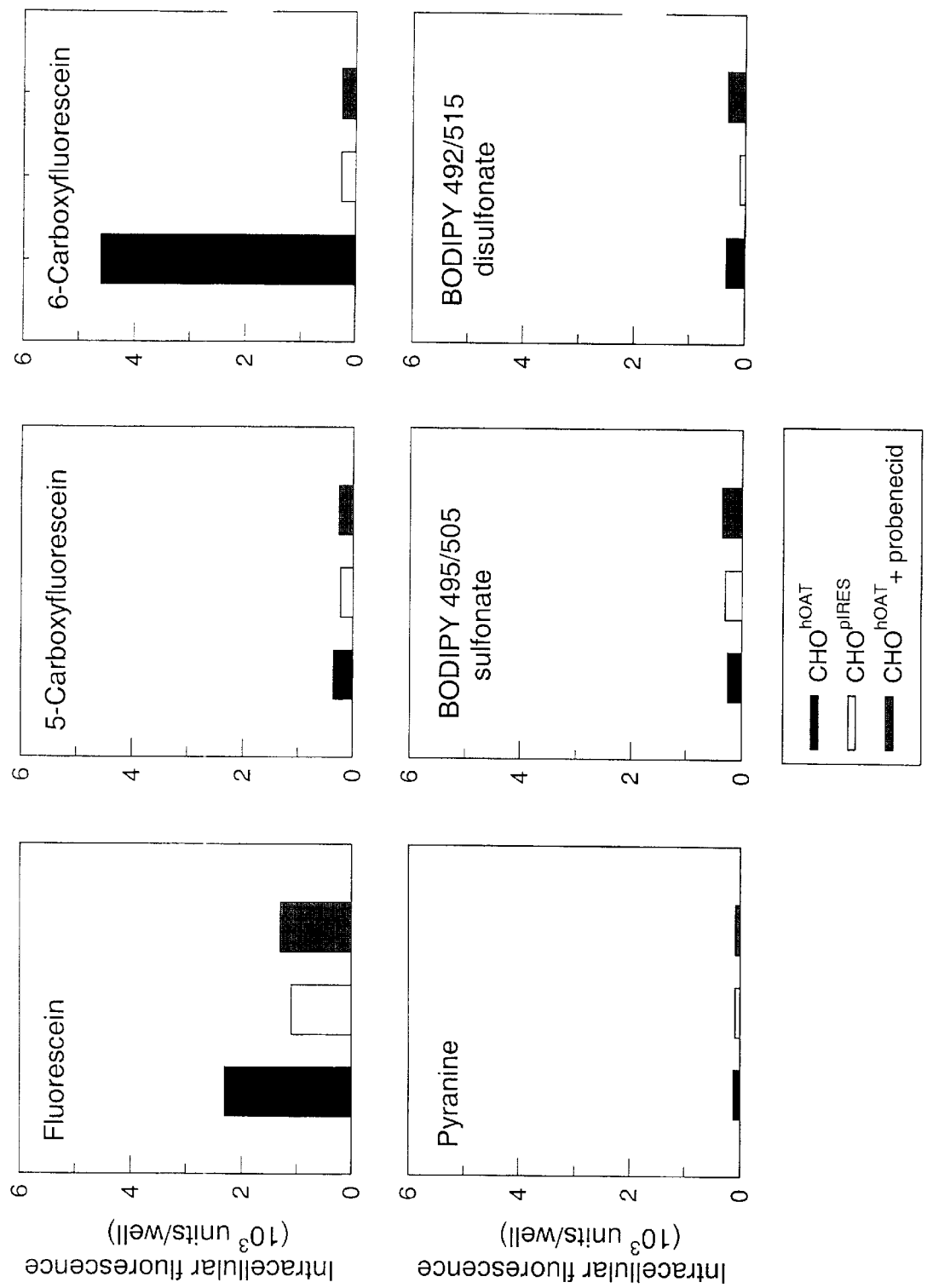

FIG. 1. Fluorescent organic anions and their characteristics.

FIG. 2. Transport of fluorescent organic anions by hOAT1. CHO$^{hOAT}$ and CHO$^{pIRES}$ cells in 96-well plates were incubated in the presence of various fluorescent anions at 10 $\mu$M concentration. Where indicated, 1 mM probenecid was added together with the tested compound. After 10 min at room temperature, the cells were washed, lysed and the cell-associated fluorescence was determined as described in the Methods. The panels show mean data from a representative experiment performed in triplicates.

FIG. 3. Calibration curve of 6-CFL fluorescent signal. Various amounts of 6-CFL ranging from 0.1 to 15 pmols were added to 150 $\mu$l cell lysis buffer and the fluorescent signal was determined. The data are means from two experiments performed in triplicates.

Figure 4:
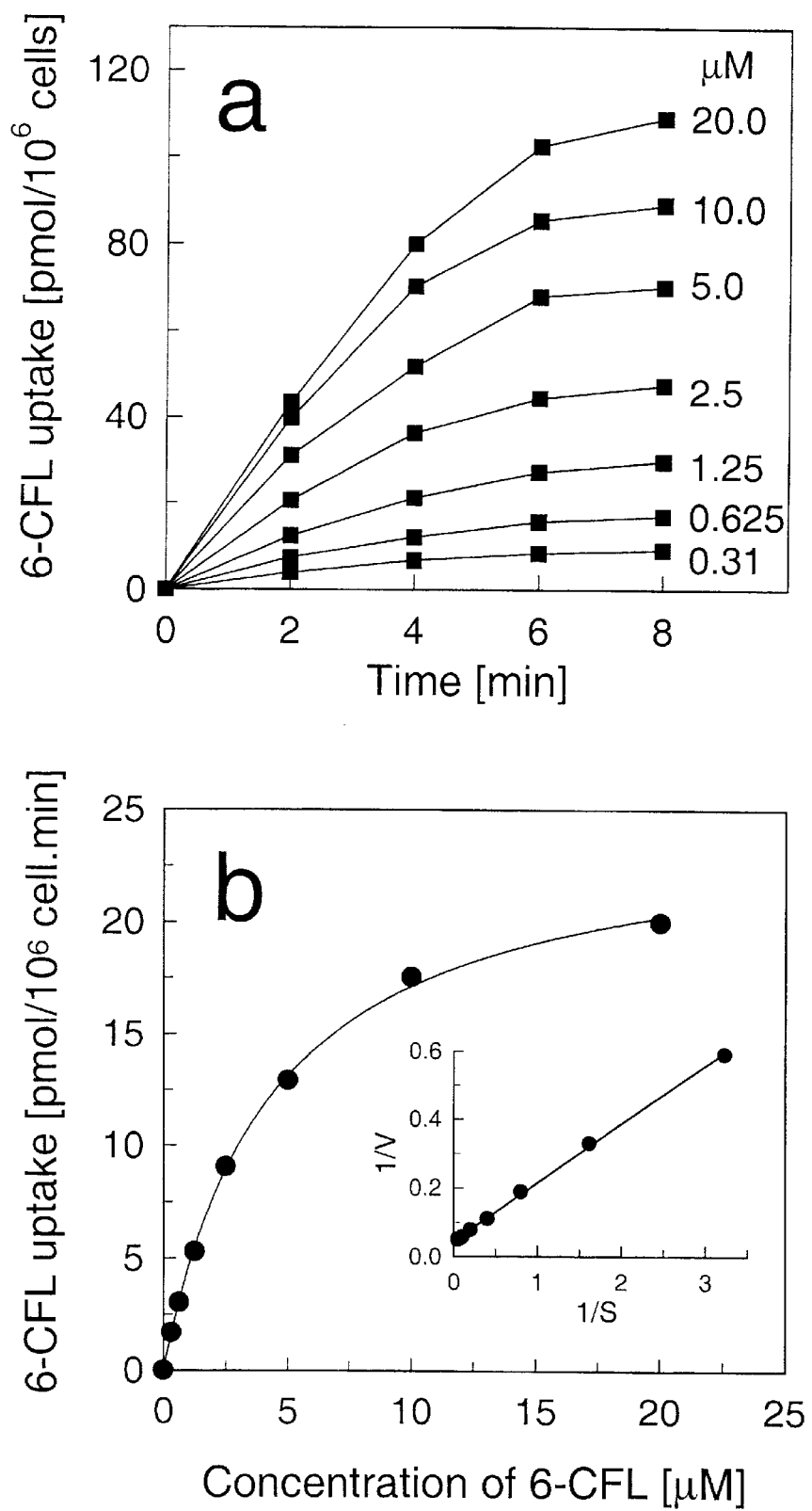

FIG. 4. Kinetics of 6-CFL transport mediated by hOAT1. (a) Time course of hOAT1-specific uptake of 6-CFL. CHO$^{pIRES}$ and CHO$^{hOAT}$ cells in 96-well plates were incubated at room temperature with 6-CFL at concentrations ranging from 0.31 to 20 $\mu$M. At specific time points, the uptake was terminated by washing the cells with ice-cold PBS. After cell lysis, the intracellular fluorescence was determined and the net hOAT1-specific uptake was calculated after the subtraction of non-specific background uptake into CHO$^{pIRES}$ cells determined under the identical conditions. The plot shows mean values from a representative experiment performed in triplicates. (b) Saturation curve of the hOAT1-specific uptake of 6-CFL at 4-min time points. $K_m$ and $V_{max}$ values were estimated from the double-reciprocal plot (inset).

FIG. 5. Stimulation of hOAT1-mediated uptake of 6-CFL by glutarate preloading. $CHO^{hOAT}$ cells were incubated in Waymouth buffer in the absence or presence of 1.25 mM glutarate for 2 hours. After extensive washing, 5-min uptake of 4 µM 6-CFL was determined as described in the Methods. The data are means±standard errors from two independent experiments performed in triplicates.

What is claimed is:

1. A method comprising contacting isolated hOAT1 with a compound having formula I

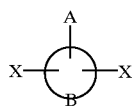

wherein A is a detectable group, B is a saturated or unsaturated heterocycle or carbocycle containing 6 ring atoms, X independently is —$(R_1)$nY, where n independently is 0 or 1, $R_1$ is —$CR_2R_3$; $R_2$ and $R_3$ independently are hydrogen, halo, nitro, or $C_1$–$C_2$ alkyl, and Y is carboxyl or aldehyde; wherein B is unsubstituted other than by X or is substituted with X and with $R_2$; and wherein the —$(R_1)$nY groups are positioned para to one another.

2. The method of claim 1 wherein the detectable group is a fluorophore or chromophore.

3. The method of claim 2 wherein the detectable group is a fluorophore.

4. The method of claim 3 wherein the detectable group is of formula II

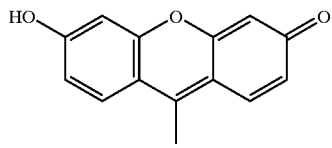

5. The method of claim 1 wherein the group

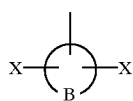

has structure III

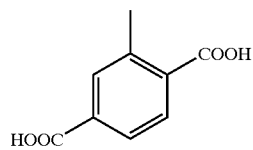

6. The method of claim 1 wherein the compound of formula I is 6-carboxyfluorescein.

7. The method of claim 1 further comprising contacting hOAT1 with a test sample in the presence of a compound of formula I.

8. The method of claim 1 wherein the hOAT1 is recombinantly expressed in CHO cells.

9. The. method of claim 1 wherein the test sample is suspected to contain a nephrotoxic or nephroprotectant substance.

10. The method of claim 1 wherein the hOAT1 is contacted with the compound of formula I in cell culture or in vitro.

11. The method of claim 1 wherein the test sample contains at least two test substances.

12. The method of claim 11 wherein (a) one test substance and the compound of formula I are contacted with hOAT1, (b) at least two test substances and the compound of formula I are contacted with hOAT1, and (c) the interaction between the test substances with hOAT1 individually and with hOAT1 together, are determined.

13. The method of claim 1 wherein B is phenyl.

14. The method of claim 1 wherein B is phenyl or phenyl in which one ring carbon atom is substituted by O, NH, or S.

15. The method of claim 1 wherein B is carbocyclic.

16. The method of claim 15 wherein B contains 1 or 2 double bonds.

17. The method of claim 1 wherein hOAT1 is not present within primary kidney cells in which it is normally expressed.

18. The method of claim 2 wherein the fluorophore is

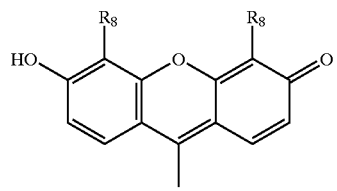

wherein $R_8$ is $R_4$ or $R_7$; $R_4$ is $C_1$–$C_3$ alkyl and $R_7$ is hydrogen or —$CH_2N(CH_2COOH)_2$;

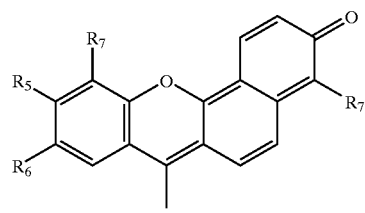

wherein $R_5$ is hydroxyl or —$N(R_4)_2$ and $R_6$ is hydrogen or halogen, $R_7$ is hydrogen or —$CH_2N(CH_2COOH)_2$; or

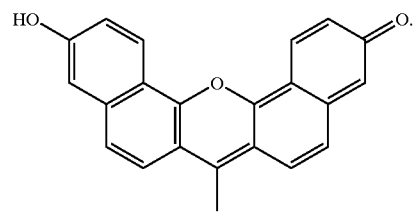

* * * * *